United States Patent [19]

Pews

[11] 4,189,572

[45] Feb. 19, 1980

[54] PREPARATION OF 1H-BENZO (2,1,3)THIADIAZINE-3,4-DIHYDRO-2,2-DIOXIDES

[75] Inventor: R. Garth Pews, Midland, Mich.

[73] Assignee: The Dow Chemical Company, Midland, Mich.

[21] Appl. No.: 973,051

[22] Filed: Dec. 15, 1978

[51] Int. Cl.$^2$ .......................................... C07D 285/16
[52] U.S. Cl. ...................................................... 544/11
[58] Field of Search ........................................... 544/11

[56] References Cited

U.S. PATENT DOCUMENTS 3,278,532  10/1966  Houlihan ................................. 544/11

OTHER PUBLICATIONS

Wright, *J. Org. Chem.*, vol. 30, pp. 3960–3962, (1965).
Knollmüller, *Monatsh. Chem.*, vol. 102, pp. 1055–1071, (1971).
Knollmüller, *Monatsh. Chem.*, vol. 101, pp. 1443–1453, (1970).

*Primary Examiner*—John M. Ford

[57] ABSTRACT

1-H-2,1,3-benzothiadiazine-3,4-dihydro-2,2-dioxides are prepared by the reaction of trioxane with N-aryl N'-alkylsulfamides in an organic solvent containing a sulfonic acid at −20° to 80° C.

4 Claims, No Drawings

PREPARATION OF 1H-BENZO (2,1,3)THIADIAZINE-3,4-DIHYDRO-2,2-DIOXIDES

BACKGROUND OF THE INVENTION

In 1965, Wright reported the first synthesis of 1H-2,1,3-benzothiadiazine-2,2-dioxides from the reaction of sulfamide with 2-aminobenzophenones and 2-aminoacetophenones. Catalytic hydrogenation of the 1H-2,1,3-benzothiadiazine-2,2-dioxides in acetic acid solution using Adams catalyst gave the 3,4-dihydroderivative; Wright, J. B., *J. Org. Chem.* 1965, 30, 3960. 1H-2,1,3-benzothiadiazine-3,4-dihydro-2,2-dioxides have also been prepared from the reaction of 2-aminobenzylamines with either sulfuryl chloride (Knollmüller, M., *Monatsh. Chem.* 1970, 101, 1443) or with sulfamide (Houlihan, William J. U.S. Patent 3,278,532, 1966 and (Knollmüller, M., *Monatsh. Chem.* 1971, 102, 1055).

SUMMARY OF THE INVENTION

In the process of this invention, 1H-2,1,3-benzothiadiazine-3,4-dihydro-2,2-dioxides, hereinafter referred to as "Compounds", (or "Compound" individually) are prepared by a novel synthesis involving cyclization by intramolecular sulfonylamidomethylation. In this synthesis, trioxane is allowed to react with an N-aryl-N'-alkylsulfamide in an organic solvent solution containing an alkyl or aryl sulfonic acid at substantially $-20°$ to $80°$ C. and preferably at ice bath to room temperature, $0°$ to $20°$ C., to provide a facile method for the preparation of Compounds. The following is a representative equation:

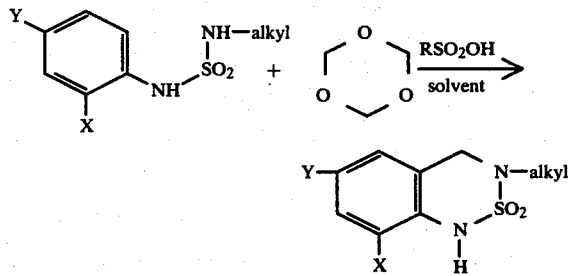

In the above equation, X represents H, $CH_3$, F, Cl, Br, $CF_3$ or $NO_2$, Y represents H, F, Cl, Br or carboethoxy and alkyl represents a 1 to 4 carbon straight or branched-chain alkyl group.

The reaction takes place when any amount of trioxane is mixed with N-aryl N'-alkylsulfamide. However, molar proportions between about 1 to 1 and about 3 to 1 and preferably 3 to 1 of sulfamide to trioxane are most advantageous since they minimize or prevent by-product formation. The reaction is usually completed in about 15 minutes to about one hour at $0°$ to $20°$ C. The reaction mixture is poured onto ice-water and washed with water to remove residual sulfonic acid. The organic extract is then dried, filtered and evaporated to give crude Compound. Recrystallization from a suitable solvent, e.g., methylene chloride-hexane, gives purified Compound.

In place of trioxane, a trimer of formaldehyde, the equivalent amount of formaldehyde, 3 moles per mole of trioxane, can be used. When used, formaldehyde is conveniently sparged into the reaction medium. As a practical matter, trioxane is more conveniently used. Since trioxane and formaldehyde are obvious equivalents in the inventive method, use of the term "trioxane" hereafter is meant to encompass formaldehyde.

The solvent mixture which is used in the reaction comprises an alkyl- or an arylsulfonate solvent or a mixture thereof, such as, for example, methanesulfonic acid, benzenesulfonic acid, toluenesulfonic acid, naphthalene sulfonic acid and mixtures thereof in combination with another organic solvent, preferably a polar organic solvent such as, for example, methylene chloride, ethylene chloride, trichloroethylene, tetrachloroethylene, chloroform, benzene, toluene and mixtures thereof, which other solvents or mixtures dissolve the sulfonic acid. The amount of solvents used is not critical. Solvent is used to dissolve the substrate. The sulfonate, which operates as a proton source, acts also as a catalyst, since the reaction to form Compounds requires an acidic medium. The amount or proportion is not critical so long as an acidic milieu is maintained.

The following examples describe representative specific embodiments and the best mode contemplated by the inventor of carrying out his inventive process. In the examples, all melting points were uncorrected. IR spectra were recorded on a Perkin Elmer 267 spectrophotometer. NMR spectra ($\delta$ expressed in parts per million) were taken on a Varian EM-360 instrument using tetramethylsilane as an internal standard.

PREPARATION A: General Procedure for the Preparation of Intermediate N-Aryl N'-(1-methylethyl)-sulfamides In a 1000 ml round-bottomed flask equipped with dropping funnel, condenser, thermometer and mechanical stirrer were placed 600 ml of methylene chloride, 38 g (0.483 mol) of pyridine and 45 g (0.483 mol) of aniline. The solution was cooled to $5°$ C. and 74 g (0.48 mol) of isopropylsulfamoyl chloride added dropwise maintaining the temperature under $10°$ C. After the addition was complete, the reaction was allowed to come to room temperature. The reaction mixture was poured into a separatory funnel and washed with water and dilute hydrochloric acid. The organic extract was dried ($MgSO_4$) and filtered. The solvent was evaporated and the crude product recrystallized. In this manner, the following sulfamides were prepared. For each, satisfactory carbon, hydrogen and nitrogen analyses were obtained. The solvent for recrystallization is given in parentheses. N-phenyl N'-(1-methylethyl)sulfamide 1a, mp $97°-98°$ C., (methylene chloride-hexane); N-tolyl N'-(1-methylethyl)sulfamide 1b, mp 104–05, (methylene chloride-hexane); N-2-fluorophenyl N'-(1-methylethyl)-sulfamide 1c, mp $89°-91°$ C., (methylene chloride-hexane); 2-chlorophenyl N'-(1-methylethyl)sulfamide 1d, mp $123°-124°$ C. (methylene chloride-hexane); N-2-bromophenyl N'-(1-methylethyl)sulfamide 1e, mp $118°-119°$ C., (methylene chloride-hexane); N-2-trifluoromethylphenyl N'-(1-methylethyl)sulfamide 1f, mp $73°-74°$ C. (benzene-hexane); N-2-nitrophenyl N'-(1-methylethyl)sulfamide 1g, mp $97°-98°$ C. (benzene-methanol); N-2-methyl-4-chlorophenyl N'-(1-methylethyl)sulfamide 1h, mp $118°-119°$ C. (methylene chloride-hexane); N-4-carboethoxyphenyl N'-(1-methylethyl)sulfamide 1i, mp $130°-32°$ C. (chloroform). Other lower alkylsulfamoyl chlorides are substituted to give analogous N'-lower alkyl substitution.

EXAMPLE 1: 1H-2,1,3-Benzothiadiazine: 3,4-dihydro-3-(1-methylethyl)-,2,2-dioxide Sulfamide 1a (26 g, 0.121 mol) was dissolved in a solution prepared from 250 mL of methylene chloride and 145 mL of methanesulfonic acid and cooled to 5° C. s-Trioxane (3.64 g, 0.04 mol) was dissolved in 100 mL of methylene chloride and added rapidly to the sulfamide solution. The temperature increased to 15° C. After the reaction was cooled to ice bath temperature, the mixture was poured onto ice-water and washed three times with water to remove residual methanesulfonic acid. The organic extract was dried (MgSO$_4$), filtered, and evaporated to give 27.7 g of crude product. Recrystallization from methylene chloride-hexane gave product mp 106°–108° C.; NMR (CDCl$_3$) δ 1.07 (d, 6, N-3 CH$_3$) 4.13 (m, 1, methine), 4.57 (s, 2, C-4), 6.50–7.25 (m, 5, aromatic and N-1).

Anal. Calcd for C$_{10}$H$_{14}$N$_2$O$_2$S: C, 53.07; H, 6.02; N, 12.38. Found: C, 53.05; H, 6.23; N, 11.96.

EXAMPLE 2: 1H-2,1,3-Benzothiadiazine: 3,4-dihydro-3-(1-methylethyl)-8-methyl-2,2-dioxide Sulfamide 1b (17.1 g, 0.075 mol) was dissolved in a solution of 90 mL methanesulfonic acid and 165 mL methylene chloride and s-trioxane (2.25 g, 0.025 mol) added in 90 mL of methylene chloride as described above to give 16.69 g of crude product. Recrystallization from methylene chloride-hexane gave product mp 134°–37° C., NMR (CDCl$_3$) δ 1.12 (d, 6, N-3 CH$_3$), 2.10 (s, 3, C-8 CH$_3$), 4.06 (m, 1, methine), 4.50 (s, 2, C-4), 6.43 (br, 1, N-1), 6.75–7.05 (m, 3, aromatic).

Anal. Calcd for C$_{11}$H$_{16}$N$_2$O$_2$S: C, 54.7; H, 6.71; N, 11.69. Found: C, 55.1; H, 6.70; N, 11.65.

EXAMPLE 3: 1H-2,1,3-Benzothiadiazine: 3,4-dihydro-3-(1-methylethyl)-8-fluoro-2,2-dioxide Sulfamide 1c (50 g, 0.215 mol) was dissolved in a solution of 475 mL of methylene chloride and 250 mL of methanesulfonic acid and s-trioxane (6.45 g, 0.072 mol) added in 175 mL of methylene chloride solution as described above to give 48 g of crude product. Recrystallization from chloroform-hexane gave product mp 127°–130° C., NMR (CDCl$_3$) δ 1.0 (d, 6, N-3 CH$_3$), 4.16 (m, 1, methine) 6.66–7.10 (m, 4, aromatic and N-1).

Anal. Calcd for C$_{10}$H$_{13}$FN$_2$O$_2$S: C, 49.16; H, 5.36; N, 11.37. Found: C, 49.31; H, 5.42; N, 11.35.

EXAMPLE 4: 1H-2,1,3-Benzothiadiazine: 3,4-dihydro-3-(1-methylethyl)-8-chloro-2,2-dioxide Sulfamide 1d, (18.6 g, 0.025 mol) was dissolved in 165 mL of methylene chloride and 90 mL of methanesulfonic acid and s-trioxane 2.25 g (0.025 mol) in 60 mL of methylene chloride added as described above to give 17.1 g of crude product. Recrystallization from benzene-methanol gave product mp 98°–100° C., NMR (CDCl$_3$) δ 1.07 (d, 6, N-3 CH$_3$), 4.03 (m, 1, methine), 4.43 (s, 2, C-4), 6.50–7.15 (m, 4, aromatic and N-1).

Anal. Calcd for C$_{10}$H$_{13}$ClN$_2$O$_2$S: C, 46.06; H, 5.02; N, 10.75. Found: C, 46.28; H, 5.20; N, 10.88.

EXAMPLE 5: 1H-2,1,3-Benzothiadiazine: 3,4-dihydro-3-(1-methylethyl)-8-bromo-2,2-dioxide Sulfamide 1e (27.7 g, 0.094 mol) was dissolved in a solution of 210 mL of methylene chloride and 110 mL of methanesulfonic acid and s-trioxane (2.82 g, 0.031 mol) added in 75 mL of methylene chloride as described above to give 26.5 g of crude product. Recrystallization from methylene chloride-hexane gave product mp 88°–89° C., NMR (CDCl$_3$) δ 1.10 (d, 6, N-3 CH$_3$) 4.17 (m, 1, methine), 4.60 (s, 2, C-4), 6.66–7.48 (m, 4, aromatic and N-1).

Anal. Calcd for C$_{10}$H$_{13}$BrN$_2$O$_2$S: C, 39.36; H, 4.35; N, 9.14. Found: C, 39.35; H, 4.29; N, 9.18.

EXAMPLE 6: 1H-2,1,3-Benzothiadiazine: 3,4-dihydro-3-(1-methylethyl)-8-trifluoromethyl-2,2-dioxide Sulfamide 1f (21.2 g, 0.075 mol) was dissolved in a solution of 165 mL of methylene chloride and 90 mL of methanesulfonic acid and s-trioxane (2.25 g, 0.025 mol) in 60 mL of methylene chloride added to give 16.7 g of crude product. Recrystallization from methanol gave product, mp 91°–93° C., NMR (CDCl$_3$) δ 1.07 (d, 6, N-3 CH$_3$), 4.10 (m, 1, methine), 4.57 (s, 2, C-4), 6.67 (b, 1, N-1), 6.80–7.4 (m, 3, aromatic).

Anal. Calcd for C$_{11}$H$_{13}$F$_3$N$_2$O$_2$S: C, 44.89; H, 4.45; N, 9.52. Found: C, 44.89; H, 4.52; N, 9.45.

EXAMPLE 7: 1H-2,1,3-Benzothiadiazine: 3,4-dihydro-3-(1-methylethyl)-8-nitro-2,2-dioxide Sulfamide 1g (20.1 g, 0.077 mol) was dissolved in a solution of 172 mL of methylene chloride and 95 mL of methanesulfonic acid and s-trioxane (2.34, 0.026 mol) in 60 mL of methylene chloride added as described above. The solution was allowed to warm to room temperature and the solution stirred for 3 hrs. and the product isolated as described above to give 17.3 g of product. Recrystallization from methanol gave product, mp 130–32: NMR (CDCl$_3$) δ 1.12 (d, 6, N-3 CH$_3$), 4.17 (m, 1 g methine) 4.73 (s, 2, C-4), 6.82–7.50 (m, 2, C-6 and C-7) 8.1 (d, 1, C-5), 9.8 (br, 1, N-1).

Anal. Calcd for C$_{10}$H$_{13}$N$_3$O$_4$S: C, 44.27; H, 4.83; N, 15.49. Found: C, 44.14; H, 4.90; N, 15.38.

EXAMPLE 8: 1H-2,1,3-Benzothiadiazine: 3,4-dihydro-3-(1-methylethyl)-6-chloro-8-methyl-2,2-dioxide Sulfamide 1h (25.0 g, 0.095 mol) was dissolved in a solution of 200 mL of methylene chloride and 115 mL of methanesulfonic acid and s-trioxane (2.88 g, 0.032 mol) added as described above to give 23.3 g of product. Recrystallization from methylene chloride-hexane gave product mp 126°–28° C., NMR (CDCl$_3$) δ 1.07 (d, 6, N-3 CH$_3$), 2.10 (s, 3, C-8 CH$_3$) 4.07 (m, 1, methine), 4.43 (s, 2, C-4) 6.5 (br, 1, N-1), 6.87 (d, 2, C-5 and C-7).

Anal. Calcd for C$_{11}$H$_{15}$ClN$_2$O$_2$S: C, 48.08; H, 5.50; N, 10.20. Found: C, 48.13; H, 5.30; N, 10.32.

EXAMPLE 9: 1H-2,1,3-Benzothiadiazine: 3,4-dihydro-3-(1-methylethyl-4-carboethoxy, ethyl ester Sulfamide 1i (15.8 g, 0.053 mol) was dissolved in 200 mL of methylene chloride and 60 mL of methanesulfonic acid and s-trioxane (1.7 g, 0.018 mol) in 20 mL of methylene chloride added as described above to give 13 g of crude product. Recrystallization from chloroform-hexane gave product mp 156°–151° C., NMR (DMSO) δ 1.10 (d, 6, N-3 CH$_3$) 1.30 (t, 3, CH$_3$-ester), 4.06 (m, 1, methine), 4.27 (g, 2, CH$_2$-ester) 6.73 (d, 1, C-8 H), 7.97 (d, 2, C-5 and C-7 H).

Anal. Calcd for C$_{13}$H$_{18}$N$_2$O$_4$S: C, 52.33; H, 6.08; N, 9.39. Found: C, 52.0; H, 6.09; N, 9.30.

EXAMPLE 10: 1H-2,1,3-Benzothiadiazine: 3,4-dihydro-3-(1-methylethyl)-6-bromo-8-methyl-2,2-dioxide The product of Example 1 (1.0 g, 4.16 mmol) and N-bromosuccinimide (0.74 g, 4.16 mmol) were dissolved in 20 mL of methyl formate and stirred at room temperature for 4 hrs. The reaction mixture was diluted with methylene chloride and washed twice with water, dried and the solvent evaporated. The crude material was recrystallized from methanol to give product mp 128°–130° C., NMR (CDCl$_3$) δ 1.12 (d, 6, N-3 CH$_3$), 4.17 (m, 1, methine), 4.60 (s, 2, C-4), 6.67–7.50 (m, 3, aromatic and N-1).

Anal. Calcd for C$_{11}$H$_{15}$N$_2$BrSO$_2$: C, 41.4; H, 4.7; N, 8.8. Found: C, 41.5; H, 4.85; N, 9.09.

EXAMPLE 11: 1H-2,1,3-Benzothiadiazine: 1-acetyl-3,4-dihydro-8-methyl-3-(1-methylethyl)-2,2-dioxide The product of Example 1 (2.4 g, 0.01 mol) and 1.4 mL of triethylamine were dissolved in 50 mL of benzene and acetyl chloride (0.78 g, 0.01 mol) in 10 mL of benzene added dropwise to the thiadiazine solution. The product was isolated by extraction and the product recrystallized from chloroform-hexane, mp 107°–109° C., NMR (CDCl$_3$) δ 1.11 (d, 6, N-3 CH$_3$), 2.03 (s, 3, C-8 CH$_3$), 2.57 (s, 3, N-1 acetyl) 4.07 (m, 1, methine), 4.27 (s, 2, C-4), 6.65–7.04 (m, 3, aromatic).

EXAMPLE 12: 1H-2,1,3-benzothiadiazine: 3,4-dihydro-3-(1-methylethyl)-6-nitro-8-methyl-2,2-dioxide The product of Example 1 (4 g, 0.17 mol) was dissolved in 100 mL of acetic acid and added dropwise to 20 mL of 70% nitric acid. After stirring for 1 hour at room temperature, the mixture was poured into water and extracted with methylene chloride. Recrystallization from chloroform-hexane gave product mp 163°–4° C., NMR (CDCl$_3$) δ 1.16 (d, 6, N-3 CH$_3$), 2.26 (s, 3, C-8), 4.17 (m, 1, methine), 4.66 (s, 2, C-4), 7.05 (br, 1, N-1), 7.76 (d, 2, C-5 and C-7).

Anal. Calcd for C$_{11}$H$_{15}$N$_3$O$_4$S: C, 46.29; H, 5.30; N, 14.73. Found: C, 45.9; H, 5.35; N, 14.70.

EXAMPLE 13: 1H-2,1,3-Benzothiadiazine: 3,4-dihydro-3-(1-methylethyl)-6-nitro-8-chloro-2,2-dioxide The compound of Example 4 (27.4 g, 0.1 mol) was dissolved in a 100 mL of glacial acetic acid and cooled to 5° C., 6.5 mL of fuming nitric acid was added dropwise maintaining the temperature below 30° C. After the addition was complete, the reaction mixture was poured into ice water and extracted with methylene chloride, dried (MgSO$_4$) and evaporated in vacuo to give 17.5 g of solids. Recrystallization from chloroform-hexane gave product mp 140°–2° C. NMR (CDCl$_3$) δ 1.06 (d, 6, N-3 CH$_3$), 4.10 (m, 1, methine), 4.63 (s, 2, C-4) 7.4 (br, 1, N-1), 7.91 (d, 2, C-5 and C-7).

Anal. Calcd for C$_{10}$H$_{12}$ClN$_3$O$_4$S: C, 39.3; H, 3.34; N, 13.83. Found: C, 39.5; H, 3.32; N, 13.84.

Compounds of this invention are taught to be useful as intermediates in the preparation of fungicidal, bactericidal and insecticidal compounds; U.S. Pat. No. 3,629,250, patented Dec. 21, 1971.

What is claimed is:

1. A method for preparing a compound corresponding to the formula

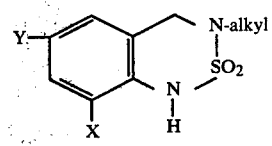

wherein an N-aryl N'-alkylsulfamide corresponding to the formula

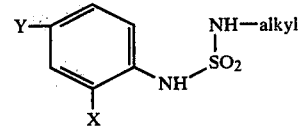

in which alkyl represents a 1 to 4 carbon straight- or branched-chain alkyl group, X represents H, CH$_3$, F, Cl, Br, CF$_3$ or NO$_2$ and Y represents H, F, Cl, Br or carboethoxy is mixed with trioxane at a temperature about −20° C. to about 80° C., in the presence of an organic sulfonic acid solvent in amount sufficient to provide an acidic reaction medium together with a solubilizing amount of another organic solvent.

2. The method of claim 1 wherein the molar proportions of sulfamide to trioxane are about 1 to 1 to about 3 to 1.

3. The method of claim 1 wherein the molar proportions of sulfamide to trioxane are about 1 to 1 to about 3 to about 1 and the reaction temperature is about 0° to 20° C.

4. The method of claim 1 wherein the molar proportions of sulfamide to trioxane are about 3 to 1, the reaction temperature is about 0° to 20° C. and the reaction solvent is a mixture of methanesulfonic acid in amount sufficient to give an acidic medium together with methylene chloride sufficient to dissolve the reactants.

* * * * *